(12) United States Patent
Dahlberg

(10) Patent No.: US 7,058,452 B2
(45) Date of Patent: Jun. 6, 2006

(54) PACEMAKER CONNECTOR PART AND MANUFACTURING PROCESS FOR MAKING SAME

(75) Inventor: Kenneth Dahlberg, Stockholm (SE)

(73) Assignee: St. Jude Medical AB (SE)

( * ) Notice: Subject to any disclaimer, the term of this patent is extended or adjusted under 35 U.S.C. 154(b) by 743 days.

(21) Appl. No.: 10/220,538

(22) PCT Filed: Jan. 29, 2001

(86) PCT No.: PCT/SE01/00164

§ 371 (c)(1),
(2), (4) Date: Aug. 30, 2002

(87) PCT Pub. No.: WO01/66184

PCT Pub. Date: Sep. 13, 2001

(65) Prior Publication Data

US 2003/0050672 A1 Mar. 13, 2003

(30) Foreign Application Priority Data

Mar. 8, 2000 (SE) .................................... 0000779

(51) Int. Cl.
*A61N 1/372* (2006.01)

(52) U.S. Cl. ............................ 607/36; 607/36; 607/37; 439/909

(58) Field of Classification Search .................. 607/36, 607/37; 439/190, 191, 909, 874
See application file for complete search history.

(56) References Cited

U.S. PATENT DOCUMENTS

| 4,262,982 | A |   | 4/1981  | Kenny |
|-----------|---|---|---------|-------|
| 4,650,271 | A | * | 3/1987  | Forney et al. ............... 439/578 |
| 4,934,366 | A | * | 6/1990  | Truex et al. ................... 607/37 |
| 4,934,966 | A |   | 6/1990  | Truex et al. |
| 5,195,910 | A | * | 3/1993  | Enomoto et al. ........... 439/578 |
| 5,324,311 | A | * | 6/1994  | Acken .......................... 607/37 |
| 6,327,502 | B1| * | 12/2001 | Johansson et al. ............ 607/36 |
| 6,816,745 | B1| * | 11/2004 | Brand et al. ................... 607/37 |

FOREIGN PATENT DOCUMENTS

| WO | WO 91/04069 | 4/1991 |
| WO | WO 00/12174 | 3/2000 |
| WO | WO 00/24462 | 5/2000 |

* cited by examiner

*Primary Examiner*—Robert E. Pezzuto
*Assistant Examiner*—Eric D. Bertram
(74) *Attorney, Agent, or Firm*—Schiff Hardin LLP

(57) ABSTRACT

In a process for manufacturing a female connector for a pacemaker, a tubular ceramic insert is formed with a longitudinal bore and with two radial holes connecting internal contact surfaces with external contact surfaces. The radial holes are filled with conductive material and the internal and external contact surfaces are metallized. The ceramic insert is covered with a layer of metal except for an area around each of the external contact surfaces.

6 Claims, 1 Drawing Sheet

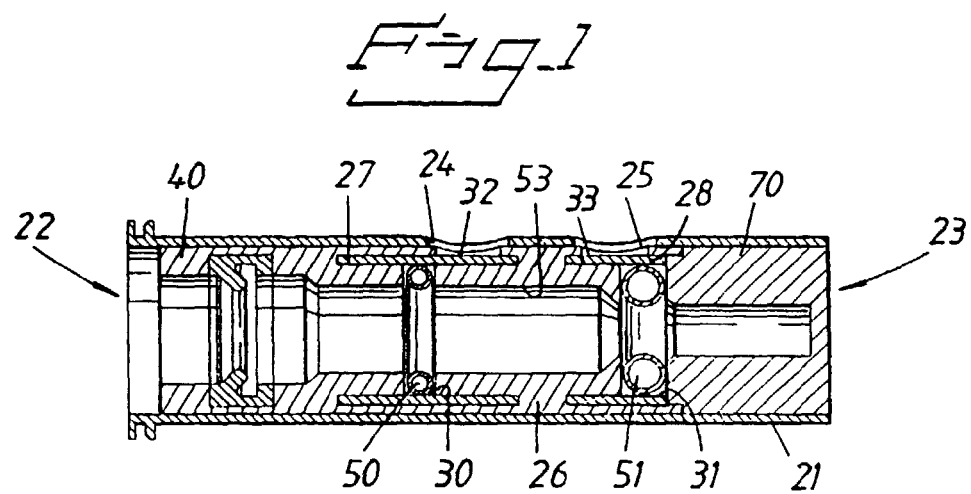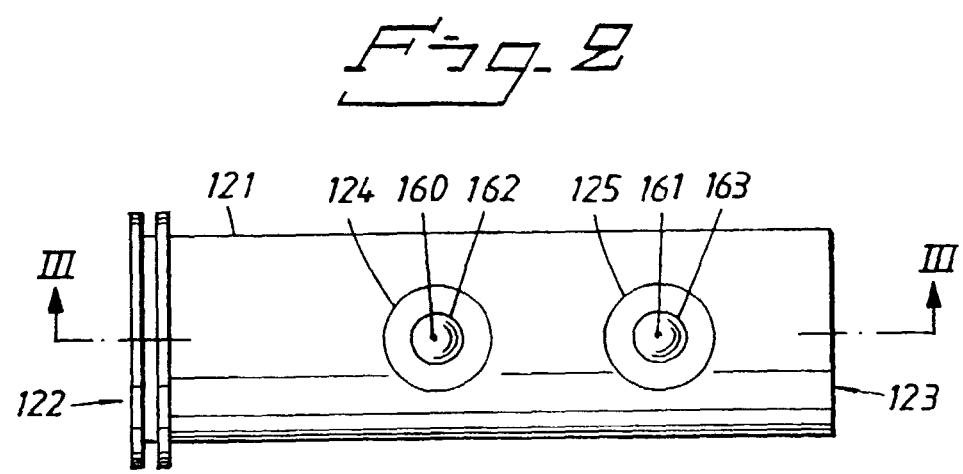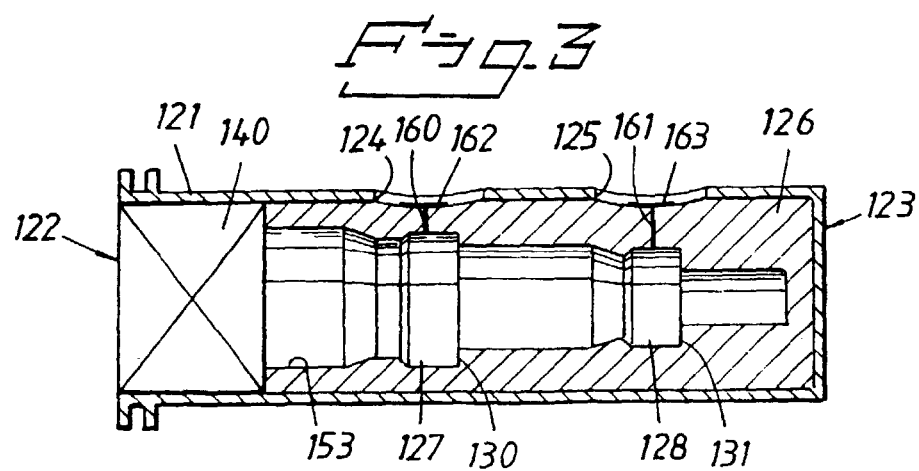

PACEMAKER CONNECTOR PART AND MANUFACTURING PROCESS FOR MAKING SAME

BACKGROUND OF THE INVENTION

1. Field of the Invention

The present invention relates to a method for manufacturing an internal connector part for a pacer, and to a female connector for pacer.

2. Description of the Prior Art

Implantable pacers normally have a pacer housing (also called can) containing electronic circuitry and a unit for electric power as well as different electrodes which are connected to the interior parts in the pacer housing and which are to be implanted in or in the vicinity of the heart. The electrodes are connected to the pacer by means of leads. The internal parts of the pacers have to be well protected against the internal environment, especially the body fluids in the body for a long period of time, which places strict requirements on all entries into the interior of the can and especially on the connections of the leads to the housing. At the same time it should be possible to disconnect the pacer from the implanted leads for replacement or servicing of the pacer. The connective parts of the pacer and the leads have largely been standardized so as to encompass a relatively deep female socket having a number of contact surfaces whereas the leads are provided with a male part having one or several corresponding peripheral, generally circular contact surfaces.

At present the connective part of the pacer housing containing the female socket is made of a transparent material, normally of epoxy resin, which is molded onto the housing and onto contacts extending outwardly from the housing. The male part of the leads is normally locked by means of set-screws, although other fastening means are known. The positioning and alignment of the different contact surfaces and the fastening means or metallic threads for the set screws prior to the molding of the connective part is, however, very complicated and the delay in the manufacturing process incurred by the curing of the epoxy resin is considerable.

It would thus be desirable if the molding procedure could be dispensed with.

It has been discussed that these complexities could be avoided by designing the pacer with a socket located inside the metal housing but this kind of socket, sometimes termed a "black hole", is not used at present.

U.S. Pat. Nos. 4,934,366 and 5,324,311, the teachings both of which are incorporated herein by reference, describe two interior sockets or black holes for pacers. Both designs have a tubular member formed by a number of alternating sections made of metal and insulating ceramic, respectively. An end section of metal can be welded or bonded to an opening in the pacer housing by means of a flange. The use of different materials however, requires high standards which regard to precision and durability of the component parts and as well as on the assembly procedure thereof. This is especially important since the interior sockets must meet very high standards regarding the integrity of the interior of the pacer housing during long times of implantation in a demanding environment. The manufacture of these prior art sockets thus is relatively complicated. The same is valid for the device disclosed in U.S. Pat. No. 4,262,982, which discloses a ceramic socket combined with a metal flange for welding to a pacer housing and with a metallic interior contact pin. This device also has locking means in the form of an inwardly directed, circumferential rib located adjacent the opening of socket. This rib is intended to cooperate with barb-shaped sealing rings on the contact plug on the proximal end of the lead or catheter.

Other connectors of the "black hole" type are disclosed in co-pending International Patent Applications No PCT/SE99/01383 (corresponding to co-pending U.S. application Ser. No. 09/763,397) and PCT/SE99/01893 (corresponding to co-pending U.S. application Ser. No. 09/830,259 filed Aug. 20, 2001). These connectors have a metallic tube containing a sintered ceramic plug with a longitudinal bore and a number of metallic contact surfaces in the form of metal rings and/or plugs molded into the ceramic materials.

SUMMARY OF THE INVENTION

It is an object of the present invention to provide a process for manufacturing a female connector for a pacemaker wherein the aforementioned disadvantages associated with known connectors are avoided.

It is a further object of the present invention to provide female connector for a pacemaker manufactured in accordance with the method.

The above object is achieved in accordance with the principles of the present invention in a process for manufacturing a female connector for a pacemaker, a tubular ceramic insert is formed with a longitudinal bore and with two radial holes connecting internal contact surfaces with external contact surfaces. The radial holes are filled with conductive material and the internal and external contact surfaces are metallized. The ceramic insert is covered with a layer of metal except for an area around each of the external contact surfaces.

The above object also is achieved in a female connector for a pacemaker having a tubular ceramic insert with a longitudinal bore and two radial holes, and internal contact surfaces and external contact surfaces. A conductive material fills the radial holes and the internal and external contact surfaces are metallized. A layer of metal covers the ceramic insert, except for an area around each of the external contact surfaces.

The ceramic insert can be inserted into a metal tube, and fixed therein by soldering or brazing.

DESCRIPTION OF THE DRAWINGS

FIG. 1 shows a connector design with a ceramic plug and concentric metal rings.

FIG. 2 shows a connector of the general type shown on FIG. 1, but manufactured in accordance with the present invention.

FIG. 3 is a section through the connector shown in FIG. 2.

DESCRIPTION OF THE PREFERRED EMBODIMENTS

FIG. 1 shows a connector of the type having a tubular member formed by a tube 21 of metal. The mid-section of the tube is provided with two relatively small lateral openings 24, 25. The openings 24, 25 are sealed by means of a ceramic plug 26 fitting snugly in the tube 21 and soldered with gold or otherwise bonded against the inside of the tube. Two contact rings 27, 28 have been molded into the ceramic plug 26.

The ceramic plug 26 is provided with an interior bore corresponding to the shape of the proximal part of a standard male connector. The ceramic plug 26 thus includes an interior sealing surface 53 for engagement with sealing rings on the male connector.

The central part 30, 31 of the inside of the contact rings 27,28 is not covered with the ceramic material. In this way two inner circumferential grooves are obtained in the inner bore of the ceramic plug 26. The bottom of the grooves consists of the metal in the contact rings. Two openings 32, 33 are also provided in the outer surface of the ceramic plug 26 that may be made to coincide with the lateral openings 24, 25 in the tube wall. These openings 24, 25 provide access to the contact rings 27, 28 when the ceramic plug has been mounted correctly in the tube 21. Leads for contacting the interior of the housing can be bonded to the parts of the contact rings 27, 28 accessible through the openings 24, 25 and 32, 33.

Thus, when the ceramic plug 26 has been soldered or bonded into place, the openings 24, 25 will be completely sealed by the plug 26 although allowing electrical connection between the interior of the tube and the interior of the housing via the contact rings 27, 28.

The inner end 23 of the tube 21 is closed by means of ceramic plug 70 soldered into the tube. The plug 70 may be made in one piece with the plug 26 or, as illustrated, in a separate piece.

The grooves 30, 31 contain spring contact rings 50, 51 of the same type as described U.S. Pat. No. 4,934,366. A locking arrangement 40 may, as illustrated, be in the form of a resilient flange intended to engage a circumferential sealing ring on the male connector or may for instance be of the type disclosed in U.S. Pat. No. 4,934,366.

FIGS. 2 and 3 illustrate a connector manufactured in accordance with the present invention. The connector has a metal tube 121 having one open end 122 and a closed end 123. The metal tube 121 contains a ceramic plug or insert 126 fitting snugly within the tube 121. In similarity with the embodiment described above, the insert 126 has a longitudinal bore, one end of which being closed. The bore also has two inner circumferential grooves 130, 131. The bottom surface of each of these grooves 130,131 is provided with a metal layer 127, 128. The metal tube 121 is provided with two lateral openings 124, 125 providing access to the outside of the ceramic insert 126. The ceramic insert 126 is provided with two holes or vias 160, 161, each connecting a respective groove 130, 131 with the outer surface of the ceramic insert exposed in the lateral openings 124, 125. The holes are filled with conductive material, thus connecting the metal layer 127, 128 in a respective groove with a respective contact 162, 163 located on the surface of the ceramic insert 126. The insert 126 is made of an insulating ceramic material such as of alumina.

In similarity with the design described in connection with FIG. 1, the connector also is provided with a space 140 intended for a means for fixing a male lead connecting part in the connector as well as an interior sealing surface 153. The grooves 130, 131 preferably each contain a spring contact ring. These parts do however not form part of the present invention and are not described in more detail.

The process according to the invention for manufacturing the above connector has the following steps:

forming and sintering a tubular ceramic insert with a longitudinal bore with a contour corresponding to a male connector, preferably a standard IS-1 male connector, the bore also being provided with internal circumferential grooves, the insert also being formed with radial holes connecting the grooves with the exterior of the insert, filling the radial holes in the insert with a conductive material, for instance by melting a solder paste into said holes metallizing the bottoms of the grooves as well as an area around each of the radial holes covering the exterior of the insert with a brazing or soldering agent with the exception of an area around each of the radial holes, for instance by metallizing or sputtering, inserting the ceramic insert into a metal tube provided with lateral openings arranged to coincide with the holes in the insert when the insert is fully inserted, brazing or soldering the insert to the inside of the metallic tube.

As is evident from the above, the manufacturing process only involves the assembly of two simple parts, namely the metal tube and the ceramic insert, both being simple to manufacture.

The ceramic insert may for instance be formed by means of hot isostatic pressing on a core or mandrel made of a polymer or at least partly made of a polymer. During the heating stage the polymer will be vaporized, thus allowing for the undercut interior grooves.

If the same material is used for contact surfaces and for soldering, the application of the soldering agent and the contact surfaces may be made in a single step.

An alternative to filling the vias with a solder paste is to solder or braze a conductor into the vias.

It is also possible to design the tube initially without the lateral openings, the openings then being obtained by grinding or abrading parts of the metal so as to uncover the ceramic material in a circular groove around the radial holes in the ceramic insert while leaving some metal in the center to serve as a contact plate.

The insertion of the ceramic insert into the metal tube can be facilitated if the tube is heated separately before the insertion of the ceramic insert. This would also allow for a very tight fit between insert and tube.

In another embodiment the metallic tube can be dispensed with if the insert is metallized to a degree that is sufficient to ensure the structural integrity of the insert.

In the above description of a preferred embodiment, the tube has been described as being open at one end only, i.e. so the connector will not go through the entire pacer housing when mounted therein. The invention is however also applicable to connectors with two opposite openings in which the space for the fixation means have been move to the opening opposite to the opening into which the male connector is to be inserted. The fixation means then would be accessible from the other end and could for instance engage the terminal end pin of the male connector. In this case, the bore in the ceramic insert would also have two opposing openings.

Although modifications and changes may be suggested by those skilled in the art, it is the invention of the inventor to embody within the patent warranted heron all changes and modifications as reasonably and properly come within the scope of his contribution to the art.

I claim as my invention:

1. A process for manufacturing a female connector for a pacemaker, comprising the steps of:

forming a tubular ceramic insert with a longitudinal bore therein, and having internal contact surfaces and external contact surfaces, and with two radial holes connecting said internal contact surfaces with said external contact surfaces;

filling said radial holes with conductive material;

metallizing said internal contact surfaces and said external contact surfaces; and covering said ceramic insert with a layer of metal except for an area around each of said external contact surfaces.

2. A process as claimed in claim 1 wherein the step of covering said ceramic insert with a layer of metal comprises covering said ceramic insert with a soldering agent, and comprising the additional steps of:

inserting said ceramic insert covered with said soldering agent into a metallic tube; and soldering said metallic tube to said ceramic insert.

3. A process as claimed in claim 1 wherein the step of covering said ceramic insert with a layer of metal comprises covering said ceramic insert with a brazing agent, and comprising the additional steps of:

inserting said ceramic insert covered with said brazing agent into a metallic tube; and brazing said metallic tube to said ceramic insert.

4. A female connector for a pacemaker, comprising:

a tubular ceramic insert having a longitudinal bore therein and having internal contact surfaces and external contact surfaces and two radial holes connecting said internal contact surfaces with said external contact surfaces;

conductive material filling said radially disposed holes;

a metallization on said internal and external contact surfaces; and a layer of metal covering said ceramic insert except for an area around each of said external contact surfaces.

5. A female connector as claimed in claim 4 wherein said layer of metal covering said ceramic insert comprises a soldering agent and said female connector further comprising a metallic tube into which said ceramic insert is inserted, said metal tube being soldered to said ceramic insert.

6. A female connector as claimed in claim 4 wherein said layer of metal covering said ceramic insert comprises a brazing agent and said female connector further comprising a metallic tube into which said ceramic insert is inserted, said metal tube being brazed to said ceramic insert.

* * * * *